United States Patent
Hosokawa et al.

(10) Patent No.: US 11,311,350 B2
(45) Date of Patent: Apr. 26, 2022

(54) RESIN CURED BODY FOR DENTAL CUTTING PROCESSING IMPROVED IN ADHESIVE PROPERTY

(71) Applicant: SHOFU INC., Kyoto (JP)

(72) Inventors: Mamoru Hosokawa, Kyoto (JP); Toshio Kitamura, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 16/145,463

(22) Filed: Sep. 28, 2018

(65) Prior Publication Data

US 2019/0192257 A1     Jun. 27, 2019

(30) Foreign Application Priority Data

Sep. 29, 2017  (JP) .............. JP2017-189787
Sep. 24, 2018  (JP) .............. JP2018-178200

(51) Int. Cl.
*A61K 6/30* (2020.01)
*A61C 5/77* (2017.01)
*A61C 13/087* (2006.01)
*A61C 13/00* (2006.01)
*A61C 13/08* (2006.01)
*A61K 6/71* (2020.01)
*A61K 6/884* (2020.01)

(52) U.S. Cl.
CPC ............ *A61C 5/77* (2017.02); *A61C 13/0022* (2013.01); *A61C 13/082* (2013.01); *A61C 13/087* (2013.01); *A61K 6/71* (2020.01); *A61K 6/884* (2020.01); *A61C 13/0004* (2013.01)

(58) Field of Classification Search
CPC . A61K 6/71; A61K 6/77; A61K 6/833; A61K 6/836; A61K 6/884; A61K 6/90; A61C 5/77; A61C 13/0022; A61C 13/082; A61C 13/087; A61C 13/0004
See application file for complete search history.

(56) References Cited

U.S. PATENT DOCUMENTS

| | | | |
|---|---|---|---|
| 5,055,497 A * | 10/1991 | Okada ............... | A61L 27/446 523/116 |
| 5,814,682 A * | 9/1998 | Rusin ................ | A61K 6/77 523/116 |
| 6,391,940 B1 * | 5/2002 | Blackwell .......... | A61K 6/20 523/115 |
| 6,984,261 B2 * | 1/2006 | Cummings ........ | C04B 35/62665 106/35 |
| 7,495,054 B2 * | 2/2009 | Lewandowski .... | A61K 6/887 524/556 |
| 2004/0077746 A1 | 4/2004 | Takeshita et al. | |
| 2006/0247330 A1 | 11/2006 | Takano et al. | |
| 2010/0068679 A1 | 3/2010 | Zappini | |
| 2018/0028413 A1 * | 2/2018 | Craig ................. | A61K 6/71 |

FOREIGN PATENT DOCUMENTS

| | | | |
|---|---|---|---|
| JP | 5-255035 | 10/1993 | |
| JP | 2016-65002 | 4/2016 | |
| JP | 2016-210710 | 12/2016 | |
| WO | WO-2016140950 A1 * | 9/2016 | .............. A61K 6/71 |

OTHER PUBLICATIONS

Montazerian, M, Zanotto, ED. 2017. Bioactive and inert dental glass-ceramics. J Biomed Mater Res Part A 2017: 105A: 619-639. (Year: 2017).*
Fu L, Engqvist H, Xia W. Glass-Ceramics in Dentistry: A Review. Materials (Basel). Feb. 26, 2020; 13(5):1049. (Year: 2020).*
Basaran, Emine Goncu et al., "Load-bearing capacity of handmade and computer-aided design-computer-aided manufacturing-fabricated three-unit fixed dental prostheses of particulate filler composite", Acta Odontologica Scandinavica, 2011, vol. 69, p. 144-150.
Extended European Search Report dated Apr. 25, 2019 in corresponding European Patent Application No. 18197879.2.

* cited by examiner

*Primary Examiner* — Sanza L. McClendon
(74) *Attorney, Agent, or Firm* — Wenderoth, Lind & Ponack, L.L.P.

(57) ABSTRACT

To provide a resin cured body for dental cutting processing used for cutting and machining using a dental CAD/CAM system, wherein the resin cured body consists of the cured body of a composition comprising:

(a) an inorganic filler containing 55 wt. % or more of an element belonging to group II and/or group XIII of the periodic table in terms of an oxide,
(b) a polymerizable monomer, and
(c) a polymerization initiator.

12 Claims, No Drawings

RESIN CURED BODY FOR DENTAL CUTTING PROCESSING IMPROVED IN ADHESIVE PROPERTY

CROSS-REFERENCE TO RELATED APPLICATIONS

This application is based on and claims the benefit of priority from Japanese Patent Application Serial No. 2017-189787 (filed on Sep. 29, 2017), the contents of which are hereby incorporated by reference in their entirety.

BACKGROUND OF THE INVENTION

Field of the Invention

The present disclosure relates to a resin cured body for dental cutting processing for preparing a tooth crown restoration which can be used as a substitute of a part of natural tooth by cutting and machining using a CAD/CAM system in the dental medical field, a tooth crown restoration using the same and an adhesion method for bonding the tooth crown restoration.

Description of the Related Art

A prosthetic treatment, in which a tooth crown restoration is prepared by casting a metal alloy and is used for restoring a defective part, is generally performed in clinical as a dental caries treatment in a dental treatment. One example of a procedure is as follows. After a cavity or an abutment tooth is formed by cutting processing the caries portion, an impression is taken. The impression mold having the taken impression is injected with a gypsum to prepare a gypsum model which reflects the formed cavity or the formed abutment tooth and to reproduce the oral cavity state. Wax-up is performed on the model using wax to reproduce a final tooth crown form. After embedding the wax pattern in an investment material, a metal crown restoration is prepared by burning up the wax pattern and casting. Finally, according to appropriate technique, after the surface treatment of the inner surface of the prepared tooth crown restoration, the prepared tooth crown restoration is set on the cavity or the abutment tooth in the oral by using an adhesive material to finalize the treatment.

A series of events from preparing a metal tooth crown restoration to mounting are above-mentioned. However, there are many materials such as ceramics or resin other than metal as the material of the tooth crown restoration. Therefore, it is usual that a dentist chooses material of the tooth crown restoration according to the oral cavity state and the portion where the tooth crown restoration is used.

Recently, hybrid resin ceramics in which various fillers such as an inorganic filler and an organic composite filler are filled at high density have been applied clinically as a tooth crown restoration. The hybrid resin ceramics are polymerized and cured by light and heating. Because a thermal polymerization is performed on the hybrid resin ceramics in addition to a photopolymerization, there are few un-polymerized resin monomers and the resin monomers are polymerized and cured at a high degree. Therefore, it is possible to prepare a tooth crown restoration having excellent aesthetic property, discoloration resistance, color tone stability and mechanical property. One example of a procedure of bonding the hybrid resin ceramics to an abutment tooth is as follows. Firstly, an inner surface of the hybrid resin ceramics prepared so as to reproduce a final tooth crown form is treated with an alumina sand blast, and water washing and drying are performed. Thereafter, the hybrid resin ceramics is treated with a primer including a silane coupling agent which can react with a surface of the inorganic filler filled in the hybrid resin ceramics (hereinafter "ceramics primer"). On the other hand, an abutment tooth is treated with a dedicated primer in accordance with the kind of a tooth substance, resin and metal or the like. Thereafter, the resin cement paste is coated on the inner surface of the hybrid resin ceramics treated with the ceramics primer, and the hybrid resin ceramics is pressure-contacted to the abutment tooth and is adhered by a photopolymerization after removing an excess paste. As described, it is necessary to use a dedicated primer in accordance with the material of a tooth crown restoration and the material of an abutment tooth, therefore the operative procedure is complex.

One example of a procedure of bonding a tooth crown restoration prepared of a hybrid resin ceramic to an abutment tooth using a resin cement paste, a primer including a silane coupling agent and a primer for a tooth substance is as follows.

(1) Alumina Sand Blast Process Step
Treating an inner surface of a tooth crown restoration with an alumina sand blast.

(2) Water Washing Process Step
Water washing the tooth crown restoration treated with the alumina sand blast.

(3) Drying Process Step
Drying the water washed tooth crown restoration.

(4) Tooth Crown Restoration Treatment Step
The dried tooth crown restoration is treated with a primer including a silane coupling agent (hereinafter "ceramics primer").

(5) Abutment Tooth Primer Treatment Step
An abutment tooth which is an adherend and is to bond the tooth crown restoration which was treated with a ceramics primer is treated with a primer (hereinafter "abutment tooth primer"). The adherend is treated with a dedicated primer in accordance with the kind of the tooth substance, resin and metal or the like.

(6) Adhesive Agent Coating Step
A resin cement paste which is an adhesive agent is applied on the inner surface of the tooth crown restoration.

(7) Abutment Tooth Pressure-Contacting Step
The tooth crown restoration of which the inner surface is coated with the resin cement paste is pressure-contacted to the abutment tooth to perform the bonding.

(8) Excess Adhesive Removing Step
Remove an excess adhesive agent which is protruded between the tooth crown restoration and the abutment tooth by pressure-contacting the tooth crown restoration to the abutment tooth.

(9) Photo Curing Step
Light is irradiated to the tooth crown restoration from which the excess adhesive agent was removed, to cure the adhesive agent and to bond the tooth crown restoration and the abutment tooth.

Recently, since a CAD/CAM system which is controlled by a computer is making remarkable advances, the CAD/CAM system has been rapidly spread in the dental field, and tooth crown restorations of various materials prepared by cutting and machining using this system have been applied clinically. In the cutting and machining using this system, a block-shaped cutting and machining material which is used for preparing an inlay and a crown and a disc-shaped cutting and machining material which is used for preparing a bridge are used. As the materials thereof ceramics materials such as zirconia ceramics, alumina ceramics and glass ceramics, metal materials such as titanium and cobalt-chromium alloy, and resin based materials such as PMMA based materials, wax, composite resin are selected and used according to an objective use and/or the needs of a patient.

Among them, because a composite resin material used for cutting processing is filled with the fillers such as an inorganic filler and an organic composite filler at high density and is polymerized and cured by pressurization heating, tooth crown restorations prepared by cutting and machining a composite resin material by the dental CAD/CAM system has more excellent aesthetic property, discoloration resistance, color tone stability and mechanical property than the above described the hybrid resin ceramics. However, on the other hand, it has been hard to exhibit the above described effect of the ceramics primer treatment. Therefore the detachment of the prosthesis due to the poor adhesion have been occurring easily.

Generally, various adhesion/luting cements, which bond a tooth crown restoration and an abutment tooth, has been developed in the dental field, and are roughly classified into a glass ionomer based cement (with no primer) and a resin based cement (set of a resin cement paste, a primer for a tooth crown restoration, and a primer for an adherend (an abutment tooth)). The former includes polycarboxylic acid, water, fluoroaluminosilicate glass as main components and the conventional glass ionomer cement and the conventional resin reinforced glass ionomer cement are included in the former. Because the operative procedure using these cements does not need a preliminary treatment of a tooth crown restoration and an abutment tooth, there are characteristics such as superior operability. However, because the adhesion mechanism is caused by the ionic bonding with the tooth crown restoration and the abutment tooth based on the ionization of polycarboxylic acid, the degree of adhesive strength is low degree and is called luting materials. Therefore, the application case has been limited by the kind of a crown restoration and an abutment tooth and it was not able to use for bonding a resin based tooth crown restoration to an abutment tooth. On the other hand, the latter includes acid polymerizable monomer, polymerizable monomer, filler as main components and a primer combined type resin cement and a self-adhesive resin cement are included in the latter. The bonds using these cements exhibit strong adhesive strength because a preliminary treatment material (primer) is used together according to the kind of a crown restoration and an abutment tooth, and therefore can be used for various application cases. Among them, although it is essential to use a primer in a primer combined type resin cement and an operative procedure of a primer combined type resin cement is complex, because a primer combined type resin cement exhibits high adhesion characteristic and stability regardless of the kind of a tooth crown restoration and an abutment tooth, a primer combined type resin cement is often used in clinical. Therefore, although a primer is required according to material to be bonded, it is recommended to use this primer combined type resin cement in bonding a tooth crown restoration which is prepared by cutting and processing by a dental CAD/CAM system from hybrid resin ceramics prepared by heating polymerization or a material for cutting and machining having a block-shape or a disc-shape prepared by pressurization heating polymerization.

As described above, there have been a situation that the kind of material of a tooth crown restoration limits an adhesion cement and a luting cement to be used for bonding, and there have been some problems such that a complex operative procedure including a combined use of a dedicated primer in accordance with the material of the tooth crown restoration is required. Therefore, the improvement of a tooth crown restoration, an adhesion cement and a luting cement has been desired. Especially, a tooth crown restoration in which various adhesion cements and luting cements are available by easy operative procedure has been desired.

Japanese Unexamined Patent Application Publication No. 2016-66002 discloses a dental curable composition in which, when a resin material for dental cutting and machining is produced while mechanical properties such as hardness, bending strength and compressive strength as well as aesthetic property required for a dental crown prosthetic appliance are maintained, strain generated in the block is reduced, and no cracks and chipping occur. However, because "ceramics primer treatment process" is required for bonding to an abutment tooth, a bonding process requires long time, therefore, it is impossible to shorten treatment time.

Japanese Unexamined Patent Application Publication No. 2016-65002 discloses a block for cutting and machining which has excellent cutting performance during cutting and machining, and has excellent impact resistance, abrasion resistance and aesthetic properties, when used in an oral cavity. However, there is still room for improvement in bonding to an abutment tooth.

SUMMARY OF THE INVENTION

Technical Problem

In the conventional tooth crown restoration which is prepared by cutting and machining a heating polymerized or pressurization heating polymerized dental cutting processing resin composition by a CAD/CAM system controlled by a computer, because the resin monomers which are components thereof are polymerized and cured at a high degree, an effect of the conventionally recommended treatment of a porcelain primer including silane coupling materials is poor, and there have been problems such as falling off in clinical use.

Therefore, one of the problem of the present disclosure is to provide a resin cured body for dental cutting processing which is prepared by a heating polymerization or a pressurization heating polymerization of the composition including specific inorganic fillers and which can bond by a simple and easy operative procedure which does not need the conventional surface treatment of a porcelain primer including silane coupling materials and uses an adhesive material containing an acidic polymerizable monomer and/or a polymer derived from the acidic polymerizable monomer, and a tooth crown restoration prepared by using the same and an adhesion method for bonding the tooth crown restoration.

In addition, another problem of the present disclosure is to bond strongly without falling off in comparison with before, when a glass ionomer based cement which does not need a primer is used for bonding.

Particularly, other problem of the present disclosure is to bond strongly without using primer when a glass ionomer based cement includes a resin based cement and a polycarboxylic acid including an acidic polymerizable monomer and/or an acidic polymerizable prepolymer derived from the acidic polymerizable monomer and/or a polymer derived from the acidic polymerizable monomer and/or the acidic polymerizable prepolymer.

Solution to Problem

The present inventors have made intensive studies in order to solve the above problem, and as a result, have found that by using an inorganic filler containing 55 wt. % or more of an element belonging to group II and/or group XIII of the periodic table in terms of an oxide as the component constructing a heating polymerized or pressurization heating polymerized dental cutting processing resin composition, a tooth crown restoration prepared by cutting and machining the dental cutting processing resin composition including the inorganic filler using a dental CAD/CAM system can bond strongly without falling off by using an adhesive material containing an acidic polymerizable monomer and/or a polymer derived from the acidic polymerizable monomer even if the conventional surface treatment of a porcelain primer including silane coupling materials is not performed, and the operative procedure is simple and easy, and have found the present disclosure.

That is, the present disclosure provides a resin cured body for dental cutting processing used for cutting and machining using a dental CAD/CAM system, wherein the resin cured body consists of the cured body of a composition comprising:
- (a) an inorganic filler containing 55 wt. % or more of an element belonging to group II and/or group XIII of the periodic table in terms of an oxide,
- (b) a polymerizable monomer, and
- (c) a polymerization initiator.

In the resin cured body for dental cutting processing of the present disclosure, it is preferable that the (a) inorganic filler and the (b) polymerizable monomer in a weight ratio of 26:75 to 80:20, and 0.1 to 2.0 parts by weight of the (c) polymerization initiator based on 100 parts by weight of the total amount of the (a) inorganic filler and the (b) polymerizable monomer.

In the resin cured body for dental cutting processing of the present disclosure, it is preferable that the (b) polymerizable monomer comprises a hydrophilic polymerizable monomer.

The present disclosure provides a tooth crown restoration prepared by cutting processing the resin cured body for dental cutting processing of the present disclosure by cutting and machining using a dental CAD/CAM system.

The present disclosure provides an adhesion method of the tooth crown restoration of the present disclosure, wherein the tooth crown restoration is bonded by using adhesive material containing an acidic polymerizable monomer and/or a polymer derived from an acidic polymerizable monomer.

Advantageous Effects of Invention

The tooth crown restoration prepared from the resin cured body for dental cutting processing of the present disclosure can simplify the adhesion operation time in clinical in the case of bonding by the resin based cement, because a tooth crown restoration treatment process is not required.

In addition, it is possible to bond strongly without falling off even if a prime is not used, when a glass ionomer based cement is used for bonding.

Particularly, it is possible to bond strongly without using primer when a glass ionomer based cement includes a resin based cement and polycarboxylic acids including an acidic polymerizable monomer and/or an acidic polymerizable prepolymer derived from the acidic polymerizable monomer and/or a polymer derived from the acidic polymerizable monomer and/or the acidic polymerizable prepolymer.

When a resin-based cement which uses a primer is used, it is possible to obtain adhesive strength like the glass ionomer cement by using a tooth substance primer for a tooth crown restoration. Furthermore, it is possible to treat a tooth crown restoration and a tooth substance with the same primer and to improve operability.

DETAILED DESCRIPTION OF THE PREFERRED EMBODIMENTS

A resin cured body for dental cutting processing of the present disclosure is a resin cured body for dental cutting processing used for cutting and machining using a dental CAD/CAM system, wherein the resin cured body consists of the cured body of a composition comprising: (a) an inorganic filler containing 55 wt. % or more of an element belonging to group II and/or group XIII of the periodic table in terms of an oxide, (b) a polymerizable monomer, and (c) a polymerization initiator.

As the (a) inorganic filler contained in the composition of the resin cured body for dental cutting processing of the present disclosure, any inorganic filler as long as the inorganic filler contains 55 wt. % or more of an element belonging to group II and/or group XIII of the periodic table in terms of an oxide can be used without any limitation. The content of the element belonging to group II and/or group XIII affects the adhesive property that is an effect of present disclosure. When the content is less than 55 wt. %, strong adhesive property is not exhibited therefore there is a risk that the falling off is caused, in the case of bonding by an adhesion cement or a luting cement. The content of the (a) inorganic filler is preferably 68 wt. % or more, and is more preferably 60 wt. % or more. Further, the content of the (a) inorganic filler is preferably 80 wt. % or less in terms of an oxide.

Examples of element belonging to group II of the periodic table included in the inorganic filler include Mg, Ca, Sr, Ba and Ra. Among them, it is preferable that at least one of Mg, Ca, Sr and Ba is included. Examples of element belonging to group XIII of the periodic table include Al, B, Ga, In and Tl. Among them, it is preferable that at least one of Al and B is included. In addition, it is preferable that the (a) inorganic filler includes at least one element belonging to group II of the periodic table and at least one element belonging to group XIII of the periodic table.

Further, it is preferable that the (a) inorganic filler includes B (boron) element as the element belonging to group XIII, because B ion is sustained released from the inorganic filler (the resin cured body for dental cutting processing). As a result, antibacterial property which prevents the adhesion of bacteria may be exhibited in addition to the improvement of the adhesive property that is an effect of present disclosure. Sustained release of the B element in the ion form from the resin cured body for dental cutting processing of the present disclosure can be confirmed by ICP emission spectrometry analysis. The content of the B element included in the inorganic filler used for the present disclosure is preferably 5 wt. % or more, more preferably 10 wt. % or more and most preferably 16 wt. % or more. The reason is because antibacterial property which prevents the adhesion of bacteria is increased by increasing sustained release property of the B element in the ion form. When the content is less than 5 wt. %, the effect is not almost recognized.

Further, it is preferable that the (a) inorganic filler includes fluorine element, because fluorine ion is sustained released from the inorganic filler (the resin cured body for dental cutting processing). As a result, the tooth substance is reinforced and the second caries are inhibited in addition to the improvement of the adhesive property that is an effect of present disclosure. Sustained release of the fluorine ion from the resin cured body for dental cutting processing of the present disclosure can be confirmed by the fluorine ion selective electrode or the ion chromatography. The content of the fluorine element included in the inorganic filler used for the present disclosure is preferably 5 wt. % or more, more preferably 10 wt. % or more and most preferably 15 wt. % or more. The reason is because the effects such as the tooth substance reinforcement and the second caries inhibition are increased by increasing sustained release property of the fluorine ion. When the content is less than 5 wt. %, the effect is not almost recognized.

Specific examples of the inorganic filler used for the present disclosure include aluminum silicate, aluminum oxide, various glasses (including a glass by a melting method, a synthetic glass by a sol-gel method, and a glass produced by a gas phase reaction), calcium carbonate, talc, kaolin, clay, mica, aluminum sulfate, calcium sulfate, barium sulfate, calcium phosphate, hydroxyapatite, aluminum nitride, boron carbide, calcium hydroxide, strontium hydroxide and zeolite, but not limited. These inorganic fillers may be used alone or in combination of two or more thereof. Among them, in order to improve adhesive property and to exhibit ion sustained release property, an aluminosilicate glass, borosilicate, aluminoborate and boroaluminosilicate glasses, and the like including strontium, barium, a heavy metal such as lanthanum, and/or fluorine are preferable.

A preparing process of the inorganic filler is not particularly limited, but an inorganic filler prepared by any process such as a melting process, a vapor phase process and a sol-gel process may be used without any problem. In addition, a shape of these inorganic filler is not particularly limited, but arbitral particle shapes such as spherical, needle-like, ground-like, and scaly-shapes may be used, and these inorganic fillers may be used alone or in combination of two or more thereof. In order to impart excellent abradability and surface lubricity property after wearing to a tooth crown restoration prepared from the resin cured body for dental cutting processing of the present disclosure, spherical or ground-like shape is preferable.

Furthermore, the average particle diameter of the inorganic filler is not particular limited, and inorganic fillers having various average particle diameters may be used. Among them, in order to impart excellent abradability and surface lubricity property after wearing to a tooth crown restoration prepared from the resin cured body for dental cutting processing of the present disclosure, an average particle diameter is preferably in the range from 0.01 to 10 µm, more preferably in the range from 0.03 to 6 µm. When an average particle diameter is less than 0.01 µm, since a specific surface area per unit weight is increased, it is hard to enhance the content of the inorganic filler in the composition of the resin cured body for dental cutting processing of the present disclosure. Therefore, there is a case that sufficient mechanical property and adhesive property are not exhibited. On the other hand, when an average particle diameter is more than 10 µm, because it is hard to prepare a uniform paste composition, and therefore, there is a case that stable performance is not exhibited.

Further, it is preferable that the inorganic filler used in the present disclosure is functionalized to highly strengthen the resin cured body for dental cutting processing including this inorganic filler, or the surface of the inorganic filler is surface-treated in order to increase ion sustained release property. Specific examples of a surface treatment material for use in the surface treatment include a surfactant, an aliphatic acid, an organic acid, an inorganic acid, a monomer, a polymer, various coupling materials, a silane compound, a metal alkoxide compound, and a partially condensed product thereof.

Among these surface treatment material, it is preferable that the inorganic filler used in the present disclosure is surface-treated with a silane coupling agent in order to highly strengthen the resin cured body for dental cutting processing of the present disclosure. Specific examples of silane coupling agent include vinyl trimethoxysilane, vinyl triethoxysilane, vinyl trichlorosilane, vinyl tri(β-methoxyethoxy)ailane, γ-methacryloxypropyl trimethoxysilane, γ-glycidoxypropyl trimethoxysilane, γ-mercaptopropyl trimethoxysilane, and γ-aminopropyl triethoxysilane.

In addition, it is preferable in order to increase ion sustained release property from the resin cured body for dental cutting processing of the present disclosure that a composite surface-treatment of the inorganic filler used in the present disclosure with using an acidic polymer and a silane compound is performed. The composite surface-treatment is a method of surface treatment with using the acidic polymer after covering the surface of the inorganic filler with the silane compound. Specific example is described in the following, but it is not limited to.

A silane compound expressed by general formula (I)

[Chemical Formula 1]

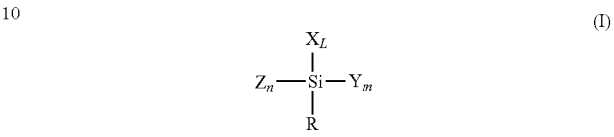

(in the formula, Z is RO—, X is halogen, Y is OH—, R is an organic group whose carbon number is less than or equal to 8, and n, m, and L are each an integer from 0 to 4 where n+m+L=4) is mixed in an aqueous dispersion containing inorganic filler finely grinded into a desired average particle diameter by grinding or the like. The surface of inorganic filler is covered with polysiloxane which is a product of hydrolysis or partial hydrolysis and condensation of the silane compound.

Specific Examples of the silane compound represented by the general formula (I) can include tetramethoxysilane, tetraethoxysilane, tetrapropoxysilane, tetraallyloxyailane, tetrabutoxysilane, tetrakis(2-ethylhexyloxy)silane, trimethoxychloroeilane, triethoxychlorosilane, triisapropoxychloroeilane, trimethoxyhydroxysilane, diethoxydichlorosilane, tetraphenoxysilane, tetrachloroeilane and silicon hydroxide (silicon oxide hydrate), more preferably tetramethoxysilane and tetraethoxysilane.

A low-condensed product of the silane compound represented by the general formula (I) is more preferable, and a low-condensed silane compound obtained by partial hydrolysis and condensation of tetramethoxysilane and tetraethoxysilane is especially preferable. Such a compound can be used singly or in combination.

The inorganic filler content in an aqueous dispersion is preferably in the range of 25 to 100 parts by weight and more preferably in the range of 30 to 75 parts by weight, with respect to 100 parts by weight of the aqueous medium which constructs the aqueous dispersion. In the case where the content of the inorganic filler exceeds 100 parts by weight, the speed of gelation by condensation is high, and a uniform polysiloxane coating layer is difficult to be formed. In the case where the content is less than 25 parts by weight, the inorganic filler may settle out in the stirring state or phase separation may occur in the aqueous medium. The addition amount of the ailane compound depends on the average particle diameter of the inorganic filler. The addition amount of the silane compound is preferably in the range of 0.1 to 10 parts by weight and more preferably in the range of 0.1 to 4 parts by weight in terms of $SiO_2$, with respect to the inorganic filler. In the case where the addition amount is less than 0.1 parts by weight, an aggregate results in crushing into primary particles may be impossible, with polysilaxane coating layer formation effect being poor. In the case where the addition amount exceeds 10 parts by weight, the solidified matter after drying may be too hard to be crushed into primary particles.

The above aqueous medium is composed of water and alcohol. The addition of alcohol has a significantly advantageous effect of reducing the aggregability of the surface coated inorganic filler during drying and improving its cracking property. The alcohol is preferably an alcohol whose carbon number is 2 to 10. In the case where an alcohol whose carbon number exceeds 10 is added, a long time is required to dry and remove the solvent due to high boiling point. Specific alcohols include ethyl alcohol, n-propyl alcohol, isopropyl alcohol, n-butyl alcohol, t-butyl alcohol, isobutyl alcohol, n-pentyl alcohol, isoamyl alcohol, n-hexyl alcohol, n-heptyl alcohol, n-octyl alcohol, and n-dodecyl alcohol. An alcohol whose carbon number is 2 to 4, such as ethyl alcohol, n-propyl alcohol, or isopropyl alcohol, is preferably used. The addition amount of the alcohol is, for example, 5 to 100 parts by weight and preferably 5 to 20 parts by weight, with respect to 100 parts by weight of water. The addition amount exceeding 100 parts by weight causes problems such as complicating the drying step.

Thereafter, a slurry which is a silane compound treated aqueous dispersion is dried to remove the aqueous media and to solidify. The drying is made up of two steps that are maturation and firing. Maturation is intended to grow the gel structure and remove the aqueous medium, and firing is intended to strengthen the gel structure. Maturation needs to be performed in a static state to keep the gel structure from distortion and remove the aqueous medium, and a facility such as a box-type hot air dryer is preferably used.

As described above, the aqueous medium is removed by drying, and a contracted solidified matter is obtained. The solidified matter is in an inorganic filler aggregate state. The solidified matter, however, is not simply an aggregate of inorganic filler, but polysiloxane formed by condensation is present on the boundary surfaces of individual fine particles. Accordingly, when the solidified matter is crushed into a size equivalent to the inorganic filler before the polysiloxane treatment in the next step, the inorganic filler whose surface is coated with polysiloxane is obtained. Here, "crushing into a size equivalent to the ion sustained release glass before the polysiloxane treatment" means crushing into primary particles of inorganic filler coated with polysiloxane. The difference from the original inorganic filler lies in that the individual fine particles are coated with polysiloxane. The inclusion of a secondary aggregate is, however, allowed to an extent that causes no problem. The solidified matter can be easily crushed by applying a shearing force or an impact force. For example, a Henschel mixer, a cross rotary mixer, a super mixer, or the like may be used for crushing.

The inorganic filler coated with polysiloxane in the above-mentioned step undergoes an acid polymer treatment of reacting with an acid polymer, as a result of which the most preferable surface-treated inorganic filler is obtained as the (a) inorganic filler. The acid polymer treatment can be made by contacting with an acid polymer solution by impregnation, spray, or the like. As an example, the inorganic filler is caused to dry flow and, in the flow state, the acid polymer solution is dispersed from above and sufficiently stirred.

The method of dispersing the acid polymer solution is not particularly limited, though dropping or spray that enables uniform dispersion is preferable. Thereafter, heat treatment is conducted. The obtained heat-treatment product may be crushed as needed to prepare a surface treated inorganic filler.

A solvent employed for preparing the acid polymer solution used in the reaction may be any solvent for dissolving the acid polymer. Examples of the solvent include water, ethanol, and acetone. Of these, water is particularly preferable. When water is used, an acid group of the acid polymer dissociates and reacts uniformly with the polysiloxane-coated inorganic filler. The weight average molecular weight of the polymer dissolved in the acid polymer solution is in the range of 2000 to 50000, and preferably in the range of 5000 to 40000. The acid polymer concentration in the acid polymer solution is preferably in the range of 3 to 25 parts by weight, and more preferably in the range of 8 to 20 parts by weight. The addition amount of the acid polymer solution to the polysiloxane-coated inorganic filler is preferably in the range of 6 to 40 parts by weight, and more preferably in the range of 10 to 30 parts by weight with respect to 100 parts by weight of the polysiloxane-coated inorganic filler. Converting this addition amount, an optimal amount of the acid polymer with respect to the polysiloxane-coated inorganic filler is in the range of 1 to 7 parts by weight, and an optimal amount of water is in the range of 10 to 25 parts by weight.

As the acid polymer that can be used to form the acid polymer reaction phase on the inside of the polysiloxane-coated inorganic filler by the method described above, any copolymers or homopolymers as long as the copolymer or homopolymer is a copolymer or homopolymer of a polymerizable monomer having an acid group such as a phosphoric acid residue, a pyrophoephoric acid residue, a thiophosphoric acid residue, a carboxylic acid residue, or a sulfonic acid group. Specific examples of the polymerizable monomer include acrylic acid, methacrylic acid, 2-chloroacrylic acid, 3-chloroacrylic acid, aconitic acid, mesaconic acid, maleic acid, itaconic acid, fumaric acid, glutaconic acid, citraconic acid, 4-(meth)acryloyloxyethoxycarbonylphthalic acid, 4-(meth)acryloyloxyethoxycarbonylphthalic anhydride, 5-(meth)acryloylaminopentylcarboxylic acid, 11-(meth)acryloyloxy-1, 1-undecanedicarboxylic acid, 2-(meth)acryloyloxyethyldihydrogenphosphate, 10-(meth)acryloyloxydecyldihydrogenphosphate, 20-(meth)acryloyloxyeicosyldihydrogenphosphate, 1,3-di(meth)acryloyloxypropyl-2-dihydrogenphosphate, 2-(meth)acryloyloxyethylphenyl phosphoric acid, 2-(meth)acryloyloxyethyl-2-bromoethyl phosphoric acid, (meth)acryloyloxyethylphenylphoephonate, di(2-(meth)acryloyloxyethylpyrophoephate, 2-(meth)acryloyloxyethyldibydrogendithiophosphate, and 10-(meth)acryloyloxydecyldihydrogenthiophosphate. Of these polymers which are (co)polymer of these polymerizable monomers, a homopolymer or a copolymer of a unsaturated carboxylic acid that is relatively slow in acid-base reaction with an acid reactive element contained in the polysiloxane-coated inorganic filler is preferable, and specific examples include an acrylic acid polymer, an acrylic acid-maleic acid copolymer, and an acrylic acid-itaconic acid copolymer.

With respect to the content of the (a) inorganic filler in the composition of the resin cured body for dental cutting processing of the present disclosure, it is preferable that the (a) inorganic filler: the (b) polymerizable monomer is in the range of =25:75 to 80:20 in the weight ratio to the (b) polymerizable monomer. The content affects the adhesive property that is an effect of present disclosure. When the content of the (a) inorganic filler is low, strong adhesive property may be not exhibited in the case of bonding by an adhesion cement or a luting cement including an acidic polymerizable monomer and/or an acidic polymerizable prepolymer derived from the acidic polymerizable monomer and/or a polymer derived from the acidic polymerizable monomer and/or the acidic polymerizable prepolymer. Therefore there is a risk that the falling off is caused. Thus, more preferable ratio of the (a) inorganic filler in the weight ratio of the (a) inorganic filler to the (b) polymerizable monomer is 30:70 or more, and further preferable is 40:60 or more.

When the content of the (a) inorganic filler exceeds 80:20 in the weight ratio of the (a) inorganic filler to the (b) polymerizable monomer, there is a case that it is hard to prepare a resin cured body for dental cutting processing in which no air bubbles are mixed.

Further, the composition of the resin cured body for dental cutting processing of the present disclosure may include other filler other than the above described (a) inorganic filler containing 55 wt. % or more of an element belonging to group II and/or group XIII of the periodic table in terms of an oxide, without any problems. Specific examples of the other filler include an inorganic filler, an organic filler and an organic inorganic composite filler which do not include an element belonging to group II and/or group XIII.

Specific examples of the other inorganic filler include a silica filler, titanium oxide, zirconium oxide, silicon nitride, titanium nitride, silicon carbide and zirconium silicate.

In addition, specific examples of the other organic filler include homopolymer and copolymer of methyl methacrylate, ethyl methacrylate, 2-ethylhexyl methacrylate, n-butyl methacrylate, i-butyl methacrylate, t-methacrylate, alkyl methacrylate, methoxyethyl methacrylate, 2-hydroxy butyl methacrylate, benzyl methacrylate, phenyl methacrylate, phenoxyethyl methacrylate and hydroxyethyl methacrylate, and a mixture of the homopolymer and the copolymer may be used.

Furthermore, the organic inorganic composite filler is a composite filler containing an inorganic filler in an organic resin. As the organic inorganic composite filler, granular materials prepared by grinding a polymer provided by polymerization of a paste which is a mixture of a monomer and an inorganic filler may be used, and the organic inorganic composite filler which is used in the conventional dental curable compositions may be used.

These various fillers may be used alone or in combination of two or more thereof.

The (b) polymerizable monomer included in the composition of the resin cured body for dental cutting processing of the present disclosure can be any of known monofunctional and polyfunctional polymerizable monomers commonly used in the field of dentistry, without any limitation. Representative examples commonly suitably used include a (meth)acrylate polymerizable monomer having an acryloyl group and/or a methacryloyl group. In the present disclosure, the term "(meth)acrylate polymerizable monomers" inclusively refers to both of an acryloyl group-containing polymerizable monomer and a methacryloyl group-containing polymerizable monomer.

Specific examples of the (b) polymerizable monomer included in the composition of the resin cured body for dental cutting processing of the present disclosure include the following.

Examples of a monofunctional polymerizable monomer include (meth)acrylic acid esters such as methyl (meth)acrylate, ethyl (meth)acrylate, butyl (meth)acrylate, hexyl (meth)acrylate, tetrahydrofurfuryl (meth)acrylate, 2-hydroxyethyl (meth)acrylate, grycidyl (meth)acrylate, lauryl (meth)acrylate, cyclohexyl (meth)acrylate, benzil (meth) acrylate, allyl (meth)acrylate, 2-ethoxyethyl (meth)acrylate, methoxy polyethylene glycol (meth)acrylate, glycerol (meth)acrylate and isobornyl (meth)acrylate; silane compounds such as Γ-(meth)acryloyloxy propyltrimethoxysilane and Γ-(meth)acryloyloxy propyltriethoxysilane; nitrogen-containing compounds such as 2-(N,N-dimethylamino) ethyl (meth)acrylate, N-methylol (meth)acrylamide and diacetone (meth)acrylamide.

Examples of an aromatic difunctional monomer include 2,2-bis (4-(meth)acryloyloxy phenyl) propane, 2,2-bis (4-(3-(meth)acryloyloxy-2-hydroxypropoxy) phenyl) propane, 2,2-bis (4-(meth)acryloyloxy ethoxyphenyl) propane, 2,2-bis (4-(meth)acryloyloxy diethoxyphenyl) propane, 2,2-bis (4-(meth)acryloyloxy tetraethoxyphenyl) propane, 2,2-bis (4-(meth)acryloyloxy pentaethoxyphenyl) propane, 2,2-bis (4-(meth)acryloyloxy dipropooxyphenyl) propane, 2-(4-(meth)acryloyloxy ethoxyphenyl)-2-(4-(meth)acryloyloxy diethoxyphenyl) propane, 2-(4-(meth)acryloyloxy diethoxyphenyl)-2-(4-(meth)acryloyloxy triethoxypheny)propane, 2-(4-(meth)acryloyloxy dipropoxyphenyl)-2-(4-(meth)acryloyloxy triethoxyphenyl)propane, 2,2-bis(4-(meth)acryloyloxy dipropoxyphenyl)propane and 2,2-bis(4-(meth)acryloyloxy isopropoxyphenyl)propane.

Examples of an aliphatic difunctional monomer include ethyleneglycoldi(meth)acrylate, diethyleneglycoldi(meth) acrylate, triethyleneglycoldi(meth)acrylate, butyleneglycoldi(meth)acrylate, neopentylglycoldi(meth)acrylate, propyleneglycoldi(meth)acrylate, polyethyleneglycoldi(meth) acrylate, 1,3-butanedioldi(meth)acrylate, 1,4-butanedioldi (meth)acrylate, 1,6-hexanedioldi(meth)acrylate and glyceroldi(meth)acrylate.

Examples of a trifunctional monomer include trimethylolpropanetri (meth) acrylate, trimethylolethanetri (meth) acrylate, trimethylolmethanetri (meth) acrylate, pentaerythritoltri (meth) acrylate, etc.

Examples of a tetrafunctional monomer include pentaerythritol tetra(meth)acrylate and ditrimethylolporpane tetra (meth)acrylate.

Examples of a urethane polymerizable monomer include di(meth)acrylates having a bifunctionality, trifunctionality or more-functionality and urethane linkage, which are derived from an adduct of a polymerizable monomer having a hydroxy group such as 2-hydroxyethyl (meth)acrylate, 2-hydroxypropyl (meth)acrylate and 3-chloro-2-hydroxypropyl (meth)acrylate, and a diisocyanate compound such methylcyclohexane diisocyanate, methylene bis(4-cyclohexyl isocyanate), hexamethylene diisocyanate, trimethyl hexamethylene diisocyanate, isophorone diisocyanate, diisocyanate methylbenzene and 4,4-diphenylmethane diisocyanate.

An oligomer or a prepolymer having at least one polymerizable group in its molecule may be used other than such a (meth)acrylate polymerizable monomer, without any limitation. There is no problem even if a substituent such as a fluoro group is contained in the same molecule.

The polymerizable monomers described above can be used not only singly but also in combinations of a plurality thereof.

Among these polymerizable monomers, it is preferable that a hydrophilic polymerizable monomer is used in the composition of the resin cured body for dental cutting processing of the present disclosure as one component of the polymerizable monomer, because sustained release property may be exhibited in addition to excellent adhesive property.

Herein, polymerizable monomers that resolve in an amount of 10 parts by weight or more in 100 parts by weight of water at 23° C. is defined as hydrophilic polymerizable monomers. The conformation method is as follows. That is, 10 g of a polymerizable monomer is added to 100 g of water kept at 23° C. in a sample bottle, and the mixture is stirred for 10 minutes to thereafter be left to stand. After the lapse of 10 minutes, the mixture in the sample bottle is observed. If the mixture is resolved uniformly transparently or translucently, the polymerizable monomer is determined as a hydrophilic polymerizable monomer.

As the hydrophilic polymerizable monomer, any polymerizable monomer as long as the polymerizable monomer exhibits hydrophilicity can be used without any limitation regardless of types of radically polymerizable unsaturated groups and in either of monofunctional and multifunctional. These hydrophilic polymerizable monomers may contain together, as far as hydrophilic, other functional group including an acidic group such as a carboxylic group, a phosphoryl group, a phosphonyl group and the like; an alkyl group; halogen; an amino group; a glycidyl group and; a hydroxide group.

Specific examples of the hydrophilic polymerizable monomer include 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammoniumethyl (meth)acrylchloride, (meth)acrylamide, 2-hydroxyethyl (meth)acrylamide, and polyethylene glycol di(meth)acrylate (the number of oxyethylene groups is greater than or equal to 9), though the hydrophilic polymerizable monomer is not limited to such.

These hydrophilic polymerizable monomers may be used singly or in combination.

With respect to the content of the (b) polymerizable monomer in the composition of the resin cured body for dental cutting processing of the present disclosure, it is preferable that the (a) inorganic filler: the (b) polymerizable monomer is in the range of =25:75 to 80:20 in the weight ratio to the (a) inorganic filler. When the content of the (b) polymerizable monomer is too large, there is a possibility that the mechanical property decreases. When the content of the (b) polymerizable monomer is too small, there are few liquid components, and therefore, it is difficult to prepare a resin cured body for dental cutting processing.

The (c) polymerization initiator included in the composition of the resin cured body for dental cutting processing of the present disclosure can be any of known polymerization initiators commonly used in the field of dentistry, without any limitation. It is preferable that the content of (c) polymerization initiator is 0.1 to 2.0 part by weight based on 100 parts by weight of the total amount of the (a) inorganic filler and the (b) polymerizable monomer. When the content of the polymerization initiator is too large, there is a case where it is hard to prepare because cracking easily occurs in preparation of the resin cured body for dental cutting processing. When the content of the polymerization initiator is too small, mechanical property may decrease because sufficient effect is not exhibited. The polymerization initiator generating a free radical is not specifically limited and any of known polymerization initiators which generate a free radical by thermolysis and are used in the field of dentistry can be used without any limitation. Specific examples of the polymerization initiator generating a free radical include an organic peroxide such as benzoyl peroxide, p-chlorobenzoyl peroxide, 2,4-dichlorobenzoyl peroxide, acetyl peroxide, lauroyl peroxide, tertiary butyl peroxide, cumene hydroperoxide, 2,5-dimethyl hexane, 2,56-dihydroperoxide, methyl ethyl ketone peroxide and tertiary butyl peroxybenzoate, an azo compound such as azobisisobutyronitrile, azobisisobutyric acid methyl, or azobiscyanovaleric, but it is not limited thereto. These polymerization initiators may be used alone or in combination of two or more thereof. The polymerization initiator may be subject to a secondary treatment such as microencapsulation, to improve preservation stability or adjust an initiation rate of polymerization without any problem.

Among these polymerization initiators, it is preferable to use benzoyl peroxide, azobisisobutyronitrile, trimethyl barbituric acid, tributylborane oxide and the like.

It is necessary that the resin cured body for dental cutting processing of the present disclosure has a shape which can be cut and machined by using a dental CAD/CAM system. However, any shape as long as the processing machine of the dental CAD/CAM system can hold can be used without any limitation. Specific examples of these shapes include a block-shape and a disc-shape, but not limited thereto, and the dimensions thereof are not particularly limited.

For example, it is preferable to mold in a block-shape or a disc-shape. Therefore, although a heating polymerization or a pressurization heating polymerization is finally performed caused by the polymerization initiator generating a free radical by thermolysis, it is preferable that a chemical polymerization which initiates the polymerization by mixing the compositions in the different forms and/or a photopolymerization which initiates the polymerization by light irradiation is compositely combined to perform preliminary polymeriztion and curing to adjust the shape in the desire shape, and thereafter, the heating polymerization or the pressurization heating polymerization is finally performed.

Examples of a chemical polymerization initiators which can be used in that include a redox-type polymerization initiator system comprising organic peroxide/amine compound, organic peroxide/amine compound/sulfinate, organic peroxide/amine compound/borate compound, and a polymerization catalyst system such as organic boron compounds, perborates, permanganates, and persulfates which initiate polymerization by reacting with oxygen or water. Further, sulfinates, borate compounds and barbituric acids can initiate polymerization in the presence of water or a polymerizable monomer having an acidic group.

Examples of the organic peroxide are not limited to, but include benzoyl peroxide, parachlorobenzoyl peroxide, 2,4-dichlorobenzoyl peroxide, acetyl peroxide, lauroyl peroxide, tertiary butyl peroxide, cumene hydroperoxide, 2,5-dimethylhexane, 2,5-dihydroperoxide, methyl ethyl ketone peroxide, and tertiary butyl peroxybenzoate. The organic peroxides can be used alone, or in a combination of a few of them.

As the amine compound, secondary or tertiary amine in which an amine group is bound to an aryl group is preferable, and examples are not limited to, but include N,N-dimethyl-p toluidine, N,N-dimethylaniline, N-β-hydroxyethyl-aniline, N,N-di(8-hydroxyethyl)-aniline, N,N-di(6-hydroxyethyl)-p-toluidine, N-methyl-aniline, and N-methyl-p-toluidine. The amine compounds may be used alone, or in combination of a few of them.

Examples of sulfinates are not limited to, but include sodium benzenesulfinate, lithium benzenesulfinate, and sodium p-toluenesulfinate. The sulfinates may be used alone, or in a combination of a few of them.

Examples of the borate compound are not limited to, but include a sodium salt, a lithium salt, a potassium salt, a magnesium salt, a tetrabutylammonium salt, and a tetramethylammonium salt of trialkylphenylboron, and trialkyl(p-fluorophenyl)boron (wherein an alkyl group is a n-butyl group, a n-octyl group, a n-dodecyl group etc.) The borate compounds may be used alone, or in a combination of few of them.

Examples of barbituric acids are not limited to, but include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,6-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-barbituric acid, 1,3-dimethyl-5-cyclopentylbarbituric acid, 1,3-dimethyl-5-cyclobexylbarbituric acid, 1,3-dimethyl-5-phenylbarbituric acid, 1-cyclohexyl-5-ethylbarbituric acid, 1-benzyl-5-phenylbarbituric acid and thiobarbituric acids, and salts thereof (particularly, alkali metals or alkali earth metals are preferable), for example, sodium 5-butylbarbiturate, sodium, 1,3,5-trimethylbarbiturate, calcium 1,3,5-trimethylbarbiturate and sodium 1-cyclohexyl-5-ethylbarbiturate. The barbiturates may be used alone, or in a combination of a few of them.

Among these chemical polymerization initiators, it is preferable to use a combination of organic peroxide/tertiary amine.

In a heating polymerization or a pressurization heating polymerization, uniform polymerization and curing of the polymerizable monomers are required in the resin cured body for dental cutting processing of the present disclosure in order to prevent cracks and chipping. Therefore, it is preferable that the composition for the resin cured body for dental cutting processing of the present disclosure includes a chain transfer agent, which can control the polymerization and curing. For the chain transfer agent, a known compound can be used without any limitation. Specific examples of the chain transfer agent include mercaptan compounds such as n-butylmercaptan and n-octylmercaptan, terpenoid compounds such as limonene, myrcene, α-terpinene, δ-terpinene, γ-terpinene, terpinolene, 6-pinene and α-pinene, and an α-methylstyrene dimer. Among these chain transfer materials, terpenoid compounds are particularly preferable. The amount of such a chain transfer agent contained in the composition for the resin cured body for dental cutting processing of the present disclosure is preferably 0.001 to 1 part by weight, particularly preferably 0.1 parts by weight or more and 0.5 parts by weight or less based on 100 parts by weight of the polymerizable monomer.

To the composition for the resin cured body for dental cutting processing of the present disclosure, a component such as an ultraviolet absorber such as 2-hydroxy-4-methylbenzophenone, a polymerization inhibitor such as hydroquinone, hydroquinone monomethyl ether or 2,5-ditert-butyl-4-methylphenol, a discoloration inhibitor, an antibacterial material, a coloring pigment, or other conventionally known additive can be if necessary added arbitrarily in accordance with purposes.

The resin cured body for dental cutting processing of the present disclosure is finally molded into a shape by a heating polymerization or a pressurization heating polymerization, and a molding condition and a molding method such as temperature or pressure are not particularly limited and any molding conditions and molding methods can be used.

The kind of a tooth crown restoration prepared by cutting and machining using a dental CAD/CAM system from the resin cured body for dental cutting processing of the present disclosure is not limited without any problem, but an inlay, an onlay, a crown, a bridge are preferable.

EXAMPLES

Hereinafter, the present disclosure will be described with reference to Examples. However, the present disclosure is not limited to Examples.

TABLE 1

| Filler | Composition (wt. %) | | | | | | | | | Content of oxide (wt. %) | | | Average particle diameter (μm) | Surface treatment |
| --- | --- | --- | --- | --- | --- | --- | --- | --- | --- | --- | --- | --- | --- | --- |
| | $SiO_2$ | $Al_2O_3$ | BaO | $B_2O_3$ | SrO | $Na_2O$ | CaO | $P_2O_5$ | F | Content of oxide of Group II element | Content of oxide of Group XIII element | Content of oxide of Group II and Group XIII element | | |
| Inorganic Filler 1 | 23.8 | 16.2 | — | 10.5 | 35.6 | 3.3 | — | — | 11.6 | 35.6 | 26.7 | 62.3 | 1.2 | — |
| Inorganic Filler 2 | 25.0 | 20.0 | — | 11.0 | 32.0 | 3.0 | — | — | 9.0 | 32.0 | 31.0 | 63.0 | 2.1 | — |
| Inorganic Filler 3 | 19.8 | 19.8 | — | 11.7 | 35.0 | 3.3 | — | — | 11.4 | 35.0 | 31.5 | 66.5 | 1.3 | — |
| Inorganic Filler 4 | 23.8 | 16.2 | — | 10.5 | 35.6 | 2.3 | — | — | 11.6 | 35.6 | 26.7 | 62.3 | 1.2 | Performed |
| Inorganic Filler 5 | 25.0 | 20.0 | — | 11.0 | 32.0 | 3.0 | — | — | 9.0 | 32.0 | 31.0 | 63.0 | 2.1 | Performed |
| Inorganic Filler 6 | 19.8 | 19.8 | — | 11.7 | 35.0 | 2.3 | — | — | 11.4 | 35.0 | 31.5 | 66.5 | 1.8 | Performed |
| Inorganic Filler 7 | 30.1 | 19.5 | — | 11.9 | 24.6 | 3.3 | — | — | 11.6 | 24.6 | 31.4 | 56.0 | 3.0 | — |
| Inorganic Filler 8 | 27.3 | 19.9 | — | 12.1 | 27.0 | 2.3 | — | — | 11.4 | 27.0 | 32.0 | 59.0 | 4.2 | — |
| Other filler 1 | 100.0 | — | — | — | — | — | — | — | — | — | — | — | 2.1 | — |
| Other filler 2 | 100.0 | — | — | — | — | — | — | — | — | — | — | — | 1.6 | — |
| Other filler 3 | 32.0 | 26.0 | — | — | — | 3.0 | 17.0 | 5.0 | 11.0 | 17.0 | 26.0 | 43.0 | 2.3 | — |
| Other filler 4 | 50.0 | 10.0 | 30.0 | 10.0 | — | — | — | — | — | 30.0 | 20.0 | 50.0 | 1.0 | — |

[Preparation of Inorganic Filler]

(1) Preparation of the (a) an inorganic filler containing 55 wt. % or more of an element belonging to group II and/or group XIII of the periodic table in terms of an oxide used in the present disclosure.

(Preparation of Inorganic Filler 1)

Glass materials were uniformly mixed using a ball mill to prepare a raw material mixture, and thereafter the raw material mixture was molten in a melting furnace at 1400° C. The melt was taken out from the melting furnace, and cooled in water to produce a glass (glass composition: $SiO_2$ 23.8 wt. %, $Al_2O_3$ 16.2 wt. %, $B_2O_3$ 10.5 wt. %, SrO 35.6 wt. %, $Na_2O$ 2.3 wt. %, F 11.6 wt. %). After 4 kg of alumina cobble stones having a diameter of 6 mm were loaded into an alumina pot (inner volume: 3.6 L) with a quadruple-barrel vibration mill, 500 g of the glass obtained above was loaded thereinto and pulverized for 40 hours, to provide Inorganic filler 1 containing 62.3 wt. % of an element belonging to group II and/or group XIII in terms of an oxide.

The Inorganic filler 1 was measured for 50% average particle diameter by a laser diffraction type particle size measuring apparatus (Microtrac SPA: NIKKISO Co., Ltd.). The result was 1.2 μm.

(Preparation of Inorganic Filler 2)

Glass materials were uniformly mixed using a ball mill to prepare a raw material mixture, and thereafter the raw material mixture was molten in a melting furnace at 1400° C. The melt was taken out from the melting furnace, and cooled in water to produce a glass (glass composition: $SiO_2$ 25.0 wt. %, $Al_2O_3$ 20.0 wt. %, $B_2O_3$ 11.0 wt. %, SrO 32.0 wt. %, $Na_2O$ 3.0 wt. %, F 9.0 wt. %). After 4 kg of alumina cobble stones having a diameter of 6 mm were loaded into an alumina pot (inner volume: 3.6 L) with a quadruple-barrel vibration mill, 500 g of the glass obtained above was loaded thereinto and pulverized for 40 hours, to provide Inorganic filler 2 containing 63.0 wt. % of an element belonging to group II and/or group XIII in terms of an oxide.

The Inorganic filler 2 was measured for 50% average particle diameter by a laser diffraction type particle size measuring apparatus (Microtrac SPA: NIKKISO Co., Ltd.). The result was 2.1 μm.

(Preparation of Inorganic Filler 3)

Glass materials were uniformly mixed using a ball mill to prepare a raw material mixture, and thereafter the raw material mixture was molten in a melting furnace at 1400° C. The melt was taken out from the melting furnace, and cooled in water to produce a glass (glass composition: $SiO_2$ 19.8 wt. %, $Al_2O_3$ 19.8 wt. %, $B_2O_3$ 11.7 wt. %, SrO 35.0 wt. %, $Na_2O$ 2.3 wt. %, F 11.4 wt. %). The glass was then grinded for 10 hours using a vibration mill, thus obtaining Inorganic filler 3 containing 66.5 wt. % of an element belonging to group II and/or group XIII in terms of an oxide.

The Inorganic filler 3 was measured for 50% average particle diameter by a laser diffraction type particle size measuring apparatus (Microtrac SPA: NIKKISO Co., Ltd.). The result was 1.3 μm.

(Preparation of Inorganic Fillers 4 to 6)

Inorganic fillers 4 to 6 are prepared by high functionalizing the Inorganic fillers 1 to 3. Any one of 500 g of the above-mentioned ion Inorganic fillers 1 to 3 and a silane compound (a low condensate of a silane compound obtained by stirring 5 g of tetramethoxysilane, 1000 g of water, and 100 g of ethanol for 2 hours at ambient temperature beforehand) were cast into a universal mixing stirrer and stirred and mixed for 90 minutes. The mixture was then heat-treated at 140° C. for 30 hours, thus obtaining the heat-treated object. The heat-treated object was crushed using a Henschel mixer, to obtain polysiloxane-coated inorganic filler. While stirring 500 g of the polysiloxane-coated inorganic filler, an acid polymer water solution (polyacrylic acid water solution, polymer concentration: 13% by weight, weight-average molecular weight: 20000, Nacalai Tesque, Inc.) was sprayed using a Henschel mixer. Heat treatment (at 100° C. for 3 hours) was then performed to manufacture the surface-treated Inorganic fillers 4 to 6.

(Preparation of Inorganic Filler 7)

Glass materials were uniformly mixed using a ball mill to prepare a raw material mixture, and thereafter the raw material mixture was molten in a melting furnace at 1400° C. The melt was taken out from the melting furnace, and cooled in water to produce a glass (glass composition: $SiO_2$ 30.1 wt. %, $Al_2O_3$ 19.5 wt. %, $B_2O_3$ 11.9 wt. %, SrO 24.6 wt. %, $Na_2O$ 2.3 wt. %, F 11.6 wt. %). The glass was then grinded for 10 hours using a vibration mill, thus obtaining Inorganic filler 7 containing 56.0 wt. % of an element belonging to group II and/or group XIII in terms of an oxide.

The Inorganic filler 7 was measured for 50% average particle diameter by a laser diffraction type particle size measuring apparatus (Microtrac SPA: NIKKISO Co., Ltd.). The result was 3.0 μm.

(Preparation of Inorganic Filler 8)

Glass materials were uniformly mixed using a ball mill to prepare a raw material mixture, and thereafter the raw material mixture was molten in a melting furnace at 1400° C. The melt was taken out from the melting furnace, and cooled in water to produce a glass (glass composition: $SiO_2$ 27.3 wt. %, $Al_2O_3$ 19.9 wt. %, $B_2O_3$ 12.1 wt. %, SrO 27.0 wt. %, $Na_2O$ 2.3 wt. %, F 11.4 wt. %). The glass was then grinded for 10 hours using a vibration mill, thus obtaining Inorganic filler 8 containing 69.0 wt. % of an element belonging to group II and/or group XIII in terms of an oxide.

The Inorganic filler 8 was measured for 50% average particle diameter by a laser diffraction type particle size measuring apparatus (Microtrac SPA: NIKKISO Co., Ltd.). The result was 4.2 μm.

(2) Other filler which does not correspond the (a) an inorganic filler containing 55 wt. % or more of an element belonging to group II and/or group XIII of the periodic table in terms of an oxide used in the present disclosure.

Following fillers are acquired or prepared and used.

(Other Filler 1)

FLX: FUSELEX X (silica filler, particle diameter=2.1 μm, Tatsumori Ltd.)

(Other Filler 2)

SOC5: Admafine SO-C5 which is a silica filler (silica filler, average particle diameter=1.6 μm, Admatechs)

(Other Filler 3)

Generally available glass (glass composition: $SiO_2$ 38.0 wt. %, $Al_2O_3$ 26.0 wt. %, CaO 17.0 wt. %, NasO 3.0 wt. %, $P_2O_3$ 5.0 wt. %, F 11.0 wt. %) was used as the alumino fluorosilicate glass. After 4 kg of alumina cobble stones having a diameter of 6 mm were loaded into an alumina pot (inner volume: 3.6 L) with a quadruple-barrel vibration mill, 500 g of the glass obtained above was loaded thereinto and pulverized for 40 hours, to provide filler.

This filler was measured for 50% average particle diameter by a laser diffraction type particle size measuring apparatus (Microtrac SPA: NIKKISO Co., Ltd.). The result was 2.3 μm.

(Other Filler 4)

Barium glass filler: GM8235 (manufactured by NEC SCHOTT Components Corporation, glass composition: $SiO_2$ 60.0 wt. %, BaO 30.0 wt. %, $B_2O_3$ 10.0 wt. %, $Al_2O_3$ 10.0 wt. %)

[Evaluation Method of Filler]

(Evaluation of Sustained Releasability of Borate Ion and Fluoride Ion)

0.1 g of the Inorganic filler 1 to 8 or other filler 1 to 4 was added to 100 g of distilled water, and stirred for 2 hour. Filtrate was collected by filtrating the solution with the analytical syringe filter (Chromatdisk 25A, pore size: 0.2 μm, GL Sciences Inc.). Borate ion and fluoride ion sustained released in the filtrate from each filler were measured. In the measurement of borate ion, the volume of the boron element was measured by using then inductively coupled plasma atomic emission spectrophotometer (ICPS-8000, Shimadzu Corporation), and the measurement was used for conversion to the borate ion to calculate the amount of sustained-release of borate ion. Calibration was performed using standard solutions of 0.1 ppm, 1 ppm, 10 ppm, and 50 ppm. In the case where the measured amount of boron elements were not within the calibration, the measurement was conducted with dilution according to need.

On the other hand, regarding fluoride ion, the fluoride ion was measured using a fluoride ion composite electrode (Model 9609, Orion Research Inc.) and an ion meter (Model 720A, Orion Research Inc.). Upon measurement, calibration was performed using standard solutions of 0.1 ppm, 1 ppm, 10 ppm, and 50 ppm. In addition, 0.5 ml of TISABIII (manufactured by Orion Research Inc) was added as an ionic strength adjustor. In the case where the measured amount of fluoride ions were not within the calibration, the measurement was conducted with dilution according to need.

TABLE 2

| | Composition | | | | | | | | | |
|---|---|---|---|---|---|---|---|---|---|---|
| | Resin composition | | | | | | | Filler compostion | | |
| | Polymerization initiator Benzoyl | Chain transfer agent | Polymerizable monomer | | | | | Ultrafine particle | | |
| Type | | | | | | | | | | |
| Material | peroxide | γ-terpinene | UDMA | TEGDMA | PEGDMA | HEMA | Total | R8200 | Filler | |
| Unit | (pts. wt) | (pts. wt) | (Mixing ratio) | | | | (pts. wt) | (pts. wt) | | (pts. wt) |
| Example 1 | 0.5 | 0.5 | 80 | 20 | — | — | 50 | 2 | Inorgnic filler 1 | 50 |
| Example 2 | 0.5 | 0.5 | 80 | 20 | — | — | 50 | 2 | Inorgnic filler 1 | 50 |
| Example 3 | 0.5 | 0.5 | 80 | 20 | — | — | 50 | 2 | Inorgnic filler 2 | 50 |
| Example 4 | 0.5 | 0.5 | 80 | 20 | — | — | 50 | 2 | Inorgnic filler 2 | 50 |
| Example 5 | 0.5 | 0.5 | 80 | 20 | — | — | 50 | 2 | Inorgnic filler 3 | 50 |
| Example 6 | 0.5 | 0.5 | 80 | 20 | — | — | 50 | 2 | Inorgnic filler 3 | 50 |
| Example 7 | 0.5 | 0.5 | 80 | 20 | — | — | 50 | 2 | Inorgnic filler 4 | 50 |
| Example 8 | 0.5 | 0.5 | 80 | 20 | — | — | 50 | 2 | Inorgnic filler 4 | 50 |
| Example 9 | 0.5 | 0.5 | 80 | 20 | — | — | 50 | 2 | Inorgnic filler 5 | 50 |
| Example 10 | 0.5 | 0.5 | 80 | 20 | — | — | 50 | 2 | Inorgnic filler 5 | 50 |
| Example 11 | 0.5 | 0.5 | 80 | 20 | — | — | 50 | 2 | Inorgnic filler 6 | 50 |
| Example 12 | 0.5 | 0.5 | 80 | 20 | — | — | 50 | 2 | Inorgnic filler 6 | 50 |
| Example 13 | 0.5 | 0.5 | 80 | 20 | — | — | 50 | 2 | Inorgnic filler 7 | 50 |
| Example 14 | 0.5 | 0.5 | 80 | 20 | — | — | 50 | 2 | Inorgnic filler 8 | 50 |
| Example 15 | 0.5 | 0.5 | 80 | 20 | — | — | 80 | 2 | Inorgnic filler 1 | 20 |
| Example 16 | 0.5 | 0.5 | 80 | 20 | — | — | 75 | 2 | Inorgnic filler 1 | 25 |
| Example 17 | 0.5 | 0.5 | 80 | 20 | — | — | 70 | 2 | Inorgnic filler 1 | 30 |
| Example 18 | 0.5 | 0.5 | 80 | 20 | — | — | 60 | 2 | Inorgnic filler 1 | 40 |
| Example 19 | 0.5 | 0.5 | 80 | 20 | — | — | 30 | 2 | Inorgnic filler 1 | 70 |
| Example 20 | 0.5 | 0.5 | 80 | 20 | — | — | 20 | 2 | Inorgnic filler 1 | 80 |
| Example 21 | 0.5 | 0.5 | 80 | 20 | — | — | 15 | 2 | Inorgnic filler 1 | 35 |
| Example 22 | 0.05 | 0.5 | 80 | 20 | — | — | 50 | 2 | Inorgnic filler 1 | 50 |
| Example 23 | 0.1 | 0.5 | 80 | 20 | — | — | 50 | 2 | Inorgnic filler 1 | 50 |
| Example 24 | 1 | 0.5 | 80 | 20 | — | — | 50 | 2 | Inorgnic filler 1 | 50 |
| Example 25 | 2 | 0.5 | 80 | 20 | — | — | 50 | 2 | Inorgnic filler 1 | 50 |
| Example 26 | 2.5 | 0.5 | 80 | 20 | — | — | 50 | 2 | Inorgnic filler 1 | 50 |
| Example 27 | 0.5 | 0.5 | 80 | — | 20 | — | 50 | 2 | Inorgnic filler 1 | 50 |
| Example 28 | 0.5 | 0.5 | 80 | — | — | 20 | 50 | 2 | Inorgnic filler 1 | 50 |
| Example 29 | 0.5 | 0 5 | 80 | — | 20 | — | 50 | 2 | Inorgnic filler 2 | 50 |
| Example 30 | 0.5 | 0.5 | 80 | — | — | 20 | 50 | 2 | Inorgnic filler 2 | 50 |
| Comparative Example 1 | 0.5 | 0.5 | 80 | 20 | — | — | 50 | 2 | Other filler 4 | 50 |
| Comparative Example 2 | 0.5 | 0.5 | 80 | 20 | — | — | 50 | 2 | Other filler 4 | 50 |
| Comparative Example 3 | 0.5 | 0.5 | 80 | 20 | — | — | 50 | 2 | Other filler 3 | 50 |
| Comparative Example 4 | 0.5 | 0.5 | 80 | 20 | — | — | 50 | 2 | Other filler 3 | 50 |
| Comparative Example 5 | 0.5 | 0.5 | 80 | 20 | — | — | 50 | 2 | Other filler 1 | 50 |
| Camparative Example 6 | 0.5 | 0.5 | 80 | 20 | — | — | 50 | 2 | Other filler 1 | 50 |
| Comparative Example 7 | 0.5 | 0.5 | 80 | 20 | — | — | 50 | 2 | Other filler 2 | 50 |
| Comparative Example 8 | 0.5 | 0.5 | 80 | 20 | — | — | 50 | 2 | Other filler 2 | 50 |

(Preparation of Resin Cured Body for Dental Cutting Processing)

Polymerizable monomer (mixed (meta) acrylate-based polymerizable monomers of UDMA (2,2,4-trimethyl hexamethylene bis(2-carbamoyloxy ethyl) dimethacrylate: hydrophobic polymerizable monomer): TEGDMA (triethylene glycol dimethacrylate: hydrophobic polymerizable monomer)=80:20 (by the weight ratio)) dissolving 0.5% by weight of benzoyl peroxide and 0.5% by weight of γ-terpinene was compounded with an ultrafine particle $SiO_2$ filler having 12 nm of average particle diameter (Aerosil R-8200, manufactured by Nippon Aerosil Co., Ltd., 2% by weight)) and the Inorganic filler 1 to 8 or other filler 1 to 4 to prepare the compositions of Examples 1 to 21 and Comparative Examples 1 to 8. The compounded amounts of compositions are shown in Table 2. Further, for the composition using a hydrophilic monomer, the compositions of Example 27 and Example 29 using mixed (meta) acrylate-based polymerizable monomers of UDMA: PEGDMA (polyethylene glycol dimethacrylate, the number of oxyethlene group is 14, hydrophilic polymerizable monomer)=80:20 (by the weight ratio) and the compositions of Example 28 and Example 30 using mixed (meta) acrylate-based polymerizable monomers of UDMA: HEMA (2-hydroxyethyl (meta) acrylate, hydrophilic polymerizable monomer)=80:20 (by the weight ratio) were prepared.

In addition, the compositions of Examples 22 to 26 in which the compounded amount of the benzoyl peroxide was changed were prepared. The compounded amounts of compositions are shown in Table 2.

These compositions were kneaded and defoamed under decompression to prepare mixtures. After filling these mixtures into a die made by aluminum, the mixtures were sandwiched between aluminum plates and performed with a vacuum trial closure. Thereafter, the mixtures was cured by conducting hot press under the condition of 95° C.-2t-10 min. Then, an additional heat treatment was performed for 8 hours at 100° C. to prepare resin cured bodies for dental cutting processing used for an adhesion test.

(Measurement Method of Mechanical Strength of the Resin Cured Body for Dental Cutting Processing)

A test piece (14 mm×4 mm×1.2 mm) was cut out from the resin cured body for dental cutting processing and was used as a test specimen after adjusting the surface with a water-resistant polishing paper (#2000). The three-point bending strength was measured by using an Instron universal tester (Instron 5567 manufactured by Instron) at a croshead speed of 1 mm/min according to ISO6872.

(Method of Durable Shear Adhesive Strength Test)

The resin cured body for dental cutting processing was cutting and machining by using a CAD/CAM system to prepare an adhesion test specimen having a columnar shape having the dimension of 4 mm (diameter) by 2 mm (height). An adhesive surface of the adhesion test specimen was alumina sandblasted with a pressure of 0.2-0.3 MPa using an alumina sandblast, then was washed with water and dried with air. On the other hand, a freshly removed bovine anterior tooth was used as a test specimen of an adherend. A mouth side surface of the tooth was polished with a water-resistant polishing paper (#600) to expose dentin flatly. The exposed dentin was used as an adhesive surface of the test specimen of the adherend.

The above described dentin as the test specimen of the adherend and the above described resin cured body for dental cutting processing having the columnar shape as the adhesion test specimen were bonded by using following cement materials to prepare an adhesion test piece. Table 3 shows the used cement materials.

(1) ResiCem Paste

The test specimen of the adherend and the adhesion test specimen were bonded by using "ResiCem" (manufactured by SHOFU Inc.) as a cement material according to the attached document. Specifically, the dentin which was the test specimen of the adherend and the resin cured body for dental cutting processing which was the adhesion test specimen were treated with the primer for tooth substance of ResiCem (acid polymerizable monomers: methacryloxy-ethyl trimellitate and anhydride thereof). Then the ResiCem paste was applied to the adhesion test specimen, the adhesion test specimen was pressure-contacted to the dentin at constant load (300 gf). After removing excess paste, light was irradiated using "Blue Shot 2" (manufactured by SHOFU Inc.) to prepare an adhesion test piece.

(2) Resiglass

The test specimen of the adherend and the adhesion test specimen were bonded by using "RESIGLASS" (manufactured by SHOFU Inc) as a cement material according to the attached document. Specifically, a mixture of RESIGLASS (acid polymerizable monomers: polyacrylic acid) was applied to the resin cured body for dental cutting processing which was the adhesion test specimen. Thereafter, the adhesion test specimen was pressure-contacted to the dentin which was the test specimen of the adherend at constant load (300 gf). After removing excess paste, an adhesion test piece was prepared by curing.

After immersion of the prepared adhesion test piece in 37° C. for 24 hours and then 2000 times of thermal cycle (4° C.<-->60° C., immersion in each temperature for 1 minute) was applied, a durable shear adhesive strength was measured. The durable shear adhesive strength was measured at 1 mm/min of crosshead speed by Instron Universal Testing Machine (Instron 5567; manufactured by Instron Corporation). The test results are shown in Table 3.

TABLE 3

| | | Filler | | Evaluation result | | |
|---|---|---|---|---|---|---|
| | | Content of oxide of Group II and Group XIII element (wt. %) | Surface treatment | Cement | | Durable shear adhesive strength (MPa) |
| | | | | ResiCem paste | RESIGLASS | |
| Example 1 | Inorgnic filler 1 | 62.3 | — | ○ | | 7.1 |
| Example 2 | Inorgnic filler 1 | 62.3 | — | | ○ | 6.3 |
| Example 3 | Inorgnic filler 2 | 63.0 | — | ○ | | 8.5 |
| Example 4 | Inorgnic filler 2 | 63.0 | — | | ○ | 7.9 |
| Example 5 | Inorgnic filler 3 | 66.5 | — | ○ | | 9.9 |
| Example 6 | Inorgnic filler 3 | 66.5 | — | | ○ | 8.9 |
| Example 7 | Inorgnic filler 4 | 62.3 | Performed | ○ | | 7.5 |
| Example 8 | Inorgnic filler 4 | 62.3 | Performed | | ○ | 6.5 |
| Example 9 | Inorgnic filler 5 | 63.0 | Performed | ○ | | 12.0 |
| Example 10 | Inorgnic filler 5 | 63.0 | Performed | | ○ | 9.0 |
| Example 11 | Inorgnic filler 6 | 66.5 | Performed | ○ | | 14.3 |
| Example 12 | Inorgnic tiller 6 | 66.5 | Performed | | ○ | 11.7 |
| Example 13 | Inorgnic filler 7 | 56.0 | — | ○ | | 6.2 |
| Example 14 | Inorgnic filler 8 | 59.0 | — | ○ | | 6.6 |
| Comparative Example 1 | Other filler 4 | 50.0 | — | ○ | | 1.8 |
| Comparative Example 2 | Other filler 4 | 50.0 | — | | ○ | 0.3 |
| Comparative Example 3 | Other filler 3 | 43.0 | — | ○ | | 4.9 |
| Comparative Example 4 | Other filler 3 | 43.0 | — | | ○ | 4.5 |
| Comparative Example 5 | Other filler 1 | — | — | ○ | | 0.3 |
| Comparative Example 6 | Other filler 1 | — | — | | ○ | 0.2 |
| Comparative Example 7 | Other filler 2 | — | — | ○ | | 0.4 |

TABLE 3-continued

| | | Filler | | Evaluation result | | |
|---|---|---|---|---|---|---|
| | | Content of oxide of Group II and Group XIII element (wt. %) | Surface treatment | Cement | | Durable shear adhesive strength (MPa) |
| | | | | ResiCem paste | RESIGLASS | |
| Comparative Example 8 | Other filler 2 | — | — | ○ | | 0.3 |

As shown in Examples 1 to 14 in Table 3, it was confirmed that an excellent result of the durable shear adhesive strength was exhibited in the adhesion test specimen prepared by cutting and machining the resin cured body for dental cutting processing, which is prepared from the composition for the resin cured body for dental cutting processing including the Inorganic filler 1 to 8, of the present disclosure. In the case where the composition for the resin cured body for dental cutting processing includes Inorganic filler 4 to 6 to which the special composite treatment was applied (Examples 7 to 12), more excellent level of durable shear adhesive strength was exhibited than the case where the composition includes Inorganic filler 1 to 3 to which the special composite treatment was not applied (Examples 1 to 6).

As shown in Comparative Examples 1 to 4 in Table 3, in the case of the other fillers 3 and 4, the inorganic filler included in the composition for the resin cured body for dental cutting contained the same element (element belonging to group II and/or group XIII of the periodic table in terms of an oxide), however, the content (in terms of an oxide) was small. Low durable shear adhesive strength to the dentin (Comparative Examples 1 to 4) was exhibited as compared with the result of Examples 1 to 14.

As shown in Examples 5 to 8 in Table 3, in the adhesion test specimen prepared by cutting and machining the resin cured body for dental cutting processing which is prepared from the composition for the resin cured body for dental cutting processing including the other filler 1 to 2 (silica filler), remarkably low level of the durable shear adhesive strength to the dentin was exhibited as compared with the result of Examples 1 to 14. In addition, there were some test specimen which fallen off before performing the adhesive test.

TABLE 4

| | | Composition | | | Evaluation result | |
|---|---|---|---|---|---|---|
| | | Filler | | | | Cement |
| | | Content of oxide of Group II and Group XIII element (wt. %) | Adding amount (pts. wt) | Preparation availability of resin cured body for dental cutting processing | Cement | Durable shear adhesive strength (MPa) |
| Example 1 | Inorgnic filler 1 | 62.3 | 50 | ○ | ResiCem paste | 7.1 |
| Example 15 | Inorgnic filler 1 | 62.3 | 20 | ○ | ResiCem paste | 5.6 |
| Example 16 | Inorgnic filler 1 | 62.3 | 25 | ○ | ResiCem paste | 6.2 |
| Example 17 | Inorgnic filler 1 | 62.3 | 30 | ○ | ResiCem paste | 6.9 |
| Example 18 | Inorgnic filler 1 | 62.3 | 40 | ○ | ResiCem paste | 7.0 |
| Example 19 | Inorgnic filler 1 | 62.3 | 70 | ○ | ResiCem paste | 7.7 |
| Example 20 | Inorgnic filler 1 | 62.3 | 80 | ○ | ResiCem paste | 7.6 |
| Example 21 | Inorgnic filler 1 | 62.3 | 85 | Gus bubbles mixing | ResiCem paste | 7.5 |

As shown in Table 4, the tendency that the durable shear adhesive strength became higher as the content of inorganic filler contained in the composition for the resin cured body for dental cutting processing became higher was confirmed.

In example 15 where the added amount of the inorganic filler contained in the composition for the resin cured body for dental cutting processing was less, the durable shear adhesive strength was slightly low.

In example 21 where the added amount of the inorganic filler contained in the composition for the resin cured body for dental cutting processing was too much, the mixing of gas bubbles was observed, and therefore it was difficult to prepare a resin cured body for dental cutting without defects.

TABLE 5

| | Composition | | | | | | | Evaluation result | | |
|---|---|---|---|---|---|---|---|---|---|---|
| | Filler composition | | | Resin composition | | | | Mechanical strength of resin cured body for dental cutting processing (Mpa) | | |
| | Filler | | Polymerization | | | | | | | |
| | Content of oxide of Group II and Group XIII element (wt. %) | Adding amount (pts. wt) | initiator Benzoyl peroxide (pts. wt) | Polymorizable monomer UDMA TEGDMA (Mixing ratio) | | Adding amount (pts. wt) | | | Cement | Durable shear adhesive strength (MPa) |
| Example 1 | Inorgnic filler 1 | 62.3 | 50 | 0.5 | 80 | 20 | 50 | 170 | ResiCem paste | 7.1 |
| Example 22 | Inorgnic filler 1 | 62.3 | 50 | 0.05 | 80 | 20 | 50 | 125 | ResiCem paste | 7.1 |
| Example 23 | Inorgnic filler 1 | 62.3 | 50 | 0.1 | 80 | 20 | 50 | 170 | ResiCem paste | 7.2 |
| Example 24 | Inorgnic filler 1 | 62.3 | 50 | 1 | 80 | 20 | 50 | 171 | ResiCem paste | 7.5 |
| Example 25 | Inorgnic filler 1 | 62.3 | 50 | 2 | 80 | 20 | 50 | 172 | ResiCem paste | 7.2 |
| Example 26 | Inorgnic filler 1 | 62.3 | 50 | 2.5 | 80 | 20 | 50 | 130 | ResiCem paste | 7.2 |

In table 6, a comparison of the test results in the case of varying the content of the polymerizabele initiator contained in the composition for the resin cured body for dental cutting processing is shown. In the case where the content of the polymerizabele initiator was small (Example 22), the tendency that the mechanical strength of the resin cured body for dental cutting processing decreased was confirmed. In the case where the content of the polymerizabele initiator was large (Example 26), the tendency that the cracking easily occurred in preparation of the resin cured body for dental cutting processing, and therefore the mechanical strength of the resin cured body for dental cutting processing decreased was confirmed.

TABLE 6

| | Composition | | | | | | | | Evaluation result | |
|---|---|---|---|---|---|---|---|---|---|---|
| | Filler composition | | | | | | | | | |
| | Filler | | Polymorizable monomer | | | | | | | Durable shear |
| | Content of oxide of Group II and Group XIII element (wt. %) | Adding amount (pts. wt) | UDMA | TEGDMA | PEGDMA (Mixing ratio) | HEMA | | Adding amount (pts. wt) | Cement | adhesive strength (MPa) |
| Example 1 | Inorgnic filler 1 | 62.3 | 50 | 80 | 20 | — | — | 50 | ResiCem paste | 7.1 |
| Example 27 | Inorgnic filler 1 | 62.3 | 50 | 80 | — | 20 | — | 50 | ResiCem paste | 8.0 |
| Example 28 | Inorgnic filler 1 | 62.3 | 50 | 80 | — | — | 20 | 50 | ResiCem paste | 7.9 |
| Example 3 | Inorgnic filler 2 | 63.0 | 50 | 80 | 20 | — | — | 50 | ResiCem paste | 8.5 |
| Example 29 | Inorgnic filler 2 | 63.0 | 50 | 80 | — | 20 | — | 50 | ResiCem paste | 9.0 |
| Example 30 | Inorgnic filler 2 | 63.0 | 50 | 80 | — | — | 20 | 50 | ResiCem paste | 8.9 |

In table 6, a comparison of the test results in the case of containing a hydrophilic polymerizable monomer in the composition for the resin cured body for dental cutting processing is shown. High durable shear adhesive strength was exhibited in the composition containing a hydrophilic polymerizable monomer (Examples 27 to 30).

TABLE 7

| | | Inorganic Filler 1 | Inorganic Filler 2 | Inorganic Filler 3 | Inorganic Filler 4 | Inorganic Filler 5 | Inorganic Filler 6 | Inorganic Filler 7 | Inorganic Filler 8 |
|---|---|---|---|---|---|---|---|---|---|
| Element concentration (ppm) | F | 12.9 | 11.3 | 12.4 | 30.7 | 31.4 | 32.1 | 12.5 | 12.4 |
| | B | 1.9 | 2.3 | 2.5 | 3.1 | 3.3 | 3.7 | 2.2 | 2.4 |
| | | Other filler 1 | | Other filler 2 | | Other filler 3 | | Other filler 4 | |
| Element concentration (ppm) | F | 0.0 | | 0.0 | | 10.1 | | 0.0 | |
| | B | 0.0 | | 0.0 | | 0.0 | | 0.8 | |

Table 7 shows the evaluation result of the evaluation of sustained releasability of borate ion and fluoride ion. As shown in Table 7, it was confirmed that a high level of the sustained release of borate ion and fluoride ion were sustained released at a high level from Inorganic fillers 1 to 8 containing boron element and fluorine element in the glass composition. Especially, it was confirmed that the amount of sustained release of borate ion and fluoride ion from Inorganic filler 4 to 6 to which the special composite treatment was applied was large. On the other hand, it was confirmed that any ions are sustained released from the other fillers 1 and 2 which are silica filler. Further, the other fillers 3 and 4 includes an element belonging to group II and/or group XIII of the periodic table as well as the inorganic filler included in the resin cured body for dental cutting processing of the present disclosure, however, the content in terms of an oxide of the element and/or other element composition was different. As a result, it was confirmed that certain level of fluoride ion was sustained released from other filler 3, however, no borate ion was sustained released. On the other hand, it was confirmed that a slight amount of borate ion was sustained released, however, no fluoride ion was sustained released.

Based upon the foregoing, it is considered that ion sustained release property from the inorganic filler included in the resin cured body for dental cutting processing promotes the improvement of the above-mentioned durable shear adhesive strength.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

What is claimed is:

1. A resin cured body for dental cutting processing used for cutting and machining using a dental CAD/CAM system, wherein the resin cured body consists of the cured body of a composition comprising:
   (a) an inorganic glass filler containing 55 wt. % or more of an element belonging to group II and/or group XIII of the periodic table in terms of an oxide based on a total amount of the (a) inorganic glass filler, wherein the (a) inorganic glass filler has a polysiloxane coating layer and an average particle diameter from 0.01 to 10 μm,
   (b) a polymerizable monomer, and
   (c) a polymerization initiator.

2. The resin cured body for dental cutting processing according to claim 1, wherein the resin cured body consists of the cured body of a composition comprising:
   the (a) inorganic glass filler and the (b) polymerizable monomer in a weight ratio of 25:75 to 80:20, and 0.1 to 2.0 parts by weight of the (c) polymerization initiator based on 100 parts by weight of the total amount of the (a) inorganic glass filler and the (b) polymerizable monomer.

3. The resin cured body for dental cutting processing according to claim 1, wherein the (b) polymerizable monomer comprises a hydrophilic polymerizable monomer.

4. A tooth crown restoration prepared by cutting processing the resin cured body for dental cutting processing according to claim 1.

5. An adhesion method of the tooth crown restoration according to claim 4, wherein the tooth crown restoration is bonded by using adhesive material containing an acidic polymerizable monomer and/or a polymer derived from an acidic polymerizable monomer.

6. The resin cured body used for cutting processing according to claim 2, wherein the (b) polymerizable monomer comprises a hydrophilic polymerizable monomer.

7. A tooth crown restoration prepared by cutting processing the resin cured body for dental cutting processing according to claim 2.

8. A tooth crown restoration prepared by cutting processing the resin cured body for dental cutting processing according to claim 3.

9. A tooth crown restoration prepared by cutting processing the resin cured body for dental cutting processing according to claim 6.

10. An adhesion method of the tooth crown restoration according to claim 7, wherein the tooth crown restoration is bonded by using adhesive material containing an acidic polymerizable monomer and/or a polymer derived from an acidic polymerizable monomer.

11. An adhesion method of the tooth crown restoration according to claim 8, wherein the tooth crown restoration is bonded by using adhesive material containing an acidic polymerizable monomer and/or a polymer derived from an acidic polymerizable monomer.

12. An adhesion method of the tooth crown restoration according to claim 9 wherein the tooth crown restoration is bonded by using adhesive material containing an acidic polymerizable monomer and/or a polymer derived from an acidic polymerizable monomer.

* * * * *